United States Patent [19]

Hirai et al.

[11] 4,064,137
[45] Dec. 20, 1977

[54] PENICILLIN AND CEPHALOSPORIN DERIVATIVES AND PROCESS FOR PREPARING THE SAME

[75] Inventors: Koichi Hirai; Yuji Iwano; Tokio Saito; Tetsuo Hiraoka; Yukichi Kishida; Takuzo Nishimura, all of Tokyo, Japan

[73] Assignee: Sankyo Company Limited, Tokyo, Japan

[21] Appl. No.: 759,640

[22] Filed: Jan. 17, 1977

[30] Foreign Application Priority Data

Jan. 21, 1976 Japan .................................. 51-5542

[51] Int. Cl.² .................. C07D 499/02; C07D 499/80
[52] U.S. Cl. ...................... 260/306.7 C; 260/239.1; 424/246; 424/270; 424/271; 544/21
[58] Field of Search .................. 260/239.1, 306.7 C

[56] References Cited

U.S. PATENT DOCUMENTS 3,240,786  3/1966  Hoover et al. ............... 260/306.7 C Primary Examiner—Gerald A. Schwartz
Attorney, Agent, or Firm—Flynn & Frishauf

[57] ABSTRACT

Novel penicillin and cephalosporin derivatives possessing interferon inducibility and represented by the formula

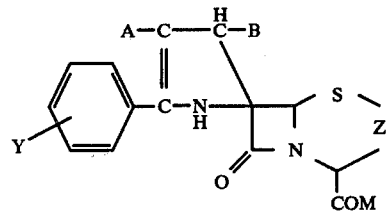

wherein Y represents a hydrogen atom, a halogen atom a nitro group, an alkoxy group or an alkyl group; M represents a protective group for a hydroxyl or carboxyl group; Z represents a group

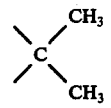

or a group

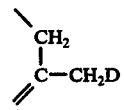

in which D is a hydrogen atom, an acyloxy group, a carbamoyloxy group or a substituted or unsubstituted heterocyclic thio group; A represents a cyano group, a carboalkoxy group or a nitro group; and B represents a hydrogen atom, a cyano group, a carboalkoxy group or a nitro group and process for preparing the same.

6 Claims, No Drawings

PENICILLIN AND CEPHALOSPORIN DERIVATIVES AND PROCESS FOR PREPARING THE SAME

The present invention relates to a novel derivative of penicillin or cephalosporin having the formula

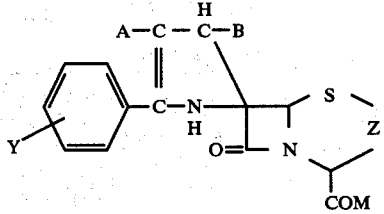

wherein Y represents a hydrogen atom, a halogen atom, a nitro group, an alkoxy group or an alkyl group; M represents a protective group for a hydroxyl or carboxyl group; Z represents a group

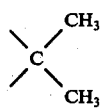

or a group

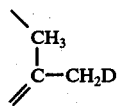

in which D is a hydrogen atom, an acyloxy group, a carbamoyloxy group or a substituted or unsubstituted heterocyclic thio group; A represents a cyano group, a carboalkoxy group or a nitro group; and B represents a hydrogen atom, a carboalkoxy group, a cyano group or a nitro group and a process for preparing the same.

Heretofore, penicillin and cephalosporin derivatives have been developed mainly as antibacterial drugs and many derivatives thereof have been synthesized.

These new derivatives of penicillin or cephalosporin have been obtained mainly by conversion of an acylamide group at the 6-position of penam nucleus or at the 7-position of cephem nucleus, or a group at the 2-position of penam nucleus or at the 3-position of cephem nucleus.

As a result of an investigation to obtain new derivatives which do not belong to the conventional penicillin or cephalosporin derivatives as mentioned above, the present inventors succeeded in obtaining entirely novel derivatives of penicillin or cephalosporin which are represented by the above formula (I) having a spiro-ring at the 6-position of penicillin nucleus or at the 7-position of cephalosporin nucleus and which are valuable compounds having interferon inducibility.

As the novel penicillin derivatives of the present invention, the following compounds may be mentioned.

3'-Cyano-2'-phenyl-2'-pyrroline-5'-spiro-6-penicillanic acid methyl ester,
3'-cyano-2'-phenyl-2'-pyrroline-5'-spiro-6-penicillanic acid benzhydryl ester,
3'-carbomethoxy-2'-phenyl-2'-pyrroline-5'-spiro-6-penicillanic acid methyl ester,
3',4'-dicarbomethoxy-2'-phenyl-2'-pyrroline-5'-spiro-6-penicillanic acid methyl ester,
3'-cyano-2'-m-chlorophenyl-2'-pyrroline-5'-spiro-6-penicillanic acid and its methyl ester,
3'-cyano-2'-o-chlorophenyl-2'-pyrroline-5'-spiro-6-penicillanic acid and its methyl ester,
3'-cyano-2'-m-bromophenyl-2'-pyrroline-5'-spiro-6-penicillanic acid and its methyl ester,
3'-cyano-2'-o-bromophenyl-2'-pyrroline-5'-spiro-6-penicillanic acid and its methyl ester,
3'-cyano-2'-m-methoxyphenyl-2'-pyrroline-5'-spiro-6-penicillanic acid and its methyl ester,
3'-cyano-2'-o-methoxyphenyl-2'-pyrroline-5'-spiro-6-penicillanic acid and its methyl ester,
3'-cyano-2'-m-nitrophenyl-2'-pyrroline-5'-spiro-6-penicillanic acid and its methyl ester,
3'-cyano-2'-o-nitrophenyl-2'-pyrroline-5'-spiro-6-penicillanic acid and its methyl ester,
3'-cyano-2'-m-methylphenyl-2'-pyrroline-5'-spiro-6-penicillanic acid and its methyl ester,
3'-cyano-2'-o-methylphenyl-2'-pyrroline-5'-spiro-6-penicillanic acid and its methyl ester,
3'-cyano-2'-m-fluorophenyl-2'-pyrroline-5'-spiro-6-penicillanic acid and its methyl ester and
3'-cyano-2'-o-fluorophenyl-2'-pyrroline-5'-spiro-6-penicillanic acid and its methyl ester.

As the novel cephalosporin derivatives, the following compounds may be mentioned.

3'-Cyano-2'-phenyl-2'-pyrroline-5'-spiro- 7-deacetylcephalosporin trichloroethyl ester,
3'-cyano-2'-phenyl-2'-pyrroline-5'-spiro-7-deacetylcephalosporin methyl ester and
3'-carbomethoxy-2'-phenyl-2'-pyrroline-5'-spiro-7-deacetylcephalosporin trichloroethyl ester.

A novel compound according to the present invention can be obtained by reacting a compound having the formula:

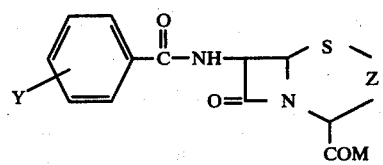

wherein Y represents a hydrogen atom, a halogen atom, a nitro group, an alkoxy group or an alkyl group; M represents a protective group for a hydroxyl or carboxyl group; Z represents a group

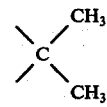

or a group

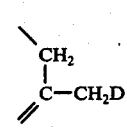

in which D is a hydrogen atom, an acyloxy group, a carbamoyloxy group or a substituted or unsubstituted heterocyclic thio group
with a halogenating agent to obtain an iminohalide compound having the formula

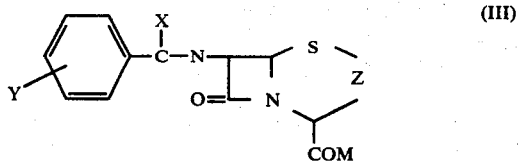

(III)

wherein X represents a halogen atom, and Y, M and Z have the same meanings as defined above
treating thus obtained compound (III) with a strong base possessing a pKa value of above 10 and then reacting with a compound having the formula

A — CH = CH — B  (IV)

wherein A represents a cyano group, a carboalkoxy group or a nitro group and B represents a hydrogen atom, a carboalkoxy group, a cyano group or a nitro group.

Among the benzoylpenicillin or benzoylcephalosporin compounds of the above formula (II) which may be used as the starting compounds in the present invention, there can preferably be used the compounds wherein Y represents a hydrogen atom, a halogen atom, an alkyl group or a nitro group; Z represents a group

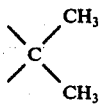

or a group

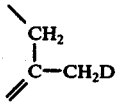

in which D is a hydrogen atom, an acetoxy group, a carbamoyloxy group, a (1-methyl-1 H-tetrazole-5-yl) thio group, a 5-methyl-3,4-thiadiazole-thio group and so on; and M represents a hydroxyl group, a methoxy group, a paramethoxybenzyloxy group, a bromophenacyloxy group, a benzhydryloxy group, a trimethylsilyloxy group, a chlorodimethylsilyloxy group and so on.

The first step of the present process is a method in which a compound of the above formula (II) is subjected to reaction with a halogenating agent to give an iminohalogenide represented by the formula (III). This step may be illustrated by the following formulas.

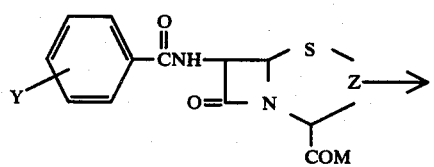
(II)

(III)

-continued

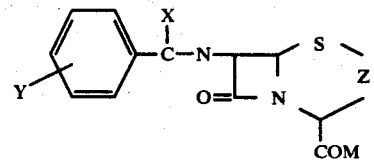

wherein M, X, Y and Z have the same meanings as defined above.

This step consists of a reaction by which a compound having an amide group at the 6- 7-position of the penam or cephem nucleus respectively is converted into an imino compound having a halogen atom.

In this reaction, the above compound (II) is reacted after dissolved in an inert solvent such as, for example, chloroform, methylene chloride, dichloroethane, etc., with a halogenating agent. As the halogenating agents employed phosphorus halogenide, sulfur halogenide, etc., may be mentioned. Particularly, phosphorus halogenide such as phosphorus pentachloride can most appropriately be used. The reaction may be conducted at a temperature of −50° to 40° C. Good results can be achieved when the reaction is conducted in the presence of a base such as organic tertiary amine, etc., e.g., quinoline, pyridine or dimethyl aniline.

In order to separate thus produced iminohalogenide having the above formula (III), the reaction mixture is subjected to evaporation in vacuo to remove the solvent.

In the second step, the iminohalogenide obtained in the first step is treated with a base such as triethylamine, triethylenediamine, 1,5-diazabicyclo[3,4,0]nonene-5 (DBN), 1,8-diazabicyclo-[5,4,0]undecene-7 (DBU), etc.

As the most preferable bases employed in this reaction there may be mentioned 1,5-diazabicyclo[3,4,0]nonene-5 (hereinafter referred to as DBN) and 1,8-diazabicyclo[5,4,0]undecene-7 (hereinafter referred to as DBU). It is considered that the iminohalogenide of the above formula (III) is converted into a 1,3-dipolar derivative by this treatment. As the solvents which may be used in this reaction, there may be mentioned hydrocarbons such as benzene, toluene, xylene, etc., and ethers such as dioxane, tetrahydrofuran, diisopropyl ether, etc. The reaction may be conducted at a temperature of −30° to 30° C, usually of −10° to 10° C. The time required for the reaction may be 10 to 60 minutes. The thus produced 1,3-dipolar derivative is provided, without isolation from the reaction mixture, for the reaction with a compound of the formula (IV) which possesses a double bond in the molecule. As the compounds of the formula (IV), there may be mentioned acrylonitrile, esters of acrylic acid, esters of maleic acid, esters of fumaric acid, nitrovinyl compounds, etc.

Since this reaction is an addition reaction, it proceeds easily immediately after adding the compound of the formula (IV) the the reaction mixture obtained in the foregoing step to give the penicilline or cephalosporin derivatives of the formula (I). After reaction, the desired compound is obtained by separation according to an ordinary method. When the desired compound is crystallized, the crystal is collected by filtration and recrystallized with a suitable solvent such as methanol, etc., to give a pure product. When the compound is not crystallizable, it is purified by treatment such as chromatography, etc.

This step is illustrated as follows.

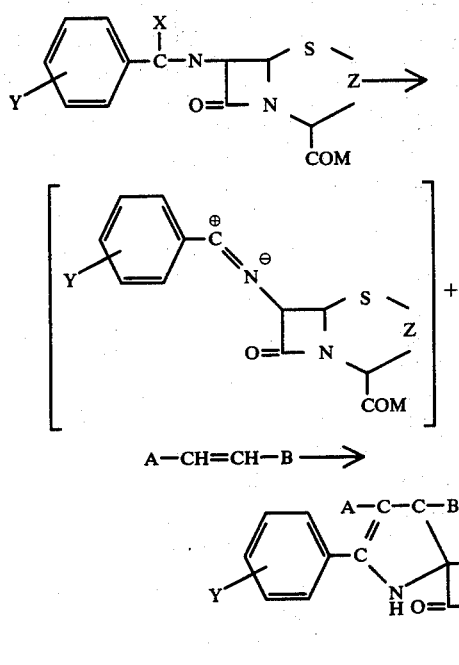

wherein A, B, M, X, Y and Z have the same meanings as defined above.

The compound of the formula (I) obtained according to the procedure mentioned above, in which M is not a hydroxyl group, is converted into a free carboxylic acid after eliminating a protective group or into a suitable nontoxic salt thereof, e.g., sodium or potassium salt, etc.

Among the compounds of the present invention, which are represented by the formula (I), there may be preferred the compounds wherein Y represents a hydrogen atom, a halogen atom, an alkoxy group or a nitro group; Z represents a group

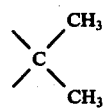

or a group

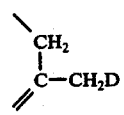

in which D is a hydrogen atom, an acetoxy group, a carbamoyloxy group, a (1-methyl-1H-tetrazole-5-yl)thio group or a 5-methyl-3,4-thiadiazolethio group; A represents a cyano group, a carboalkoxy group, or a nitro group; B represents a hydrogen atom, a cyano group or a carboalkoxy group; M represents a hydroxyl group, a methoxy group, a paramethoxybenzyloxy group, a bromophenacyloxy group, a benzhydryloxy group, a trimethylsilyloxy group or a chlorodimethylsilyloxy group.

All of the above compounds obtained according to the present invention possess interferon inducibility at a low concentration thereof and can accordingly be used as valuable ingredients for antiviral pharmaceuticals.

In practical application of the present compounds as antiviral agents, they may be administered to patients via either oral or parenteral route, preferably orally or though subcutaneous, intravenous or intramuscular injection, in various pharmaceutical preparations commonly employed for antiviral agents in the art. The present compound may be usually given in a daily dosage ranging from 50 mg to 7 g for adults, preferably 100 mg to 6 g, in a single dose or divided forms, but the dose of the present compound may be optionally varied and determined by any physicians, taking into consideration on the type and severity of a disease, the body weight and age of a patient and other factors.

Results concerning the interferon inducibility test of the compounds of the present invention will be shown below.

1. Test in Vitro

A spleen of a 6-week-old mouse was taken out and cut into strips, which were further mashed and suspended in a phosphate buffer solution. After centrifugation, the spleen cell was further suspended in Eagle's minimum essential medium (EMEM). The number of cells was counted and the suspension was diluted with EMEM so as to obtain a suspension containing $6 \times 10^8$ cells per ml. In each of glass petri dishes, 0.5 ml of the thus prepared suspension was placed. After 2.5 ml of each of diluted solutions having various concentrations of the present compound, 3'-cyano-2'-phenyl-2'-pyrroline-5'-spiro-6-penicillanic acid methyl ester was added to each of the above-mentioned petri dishes to bring the compound into contact with spleen cells of a mouse, the mixture was incubated for 20 hours. The supernatants obtained after centrifugation of the incubated mixtures were submitted to the measurement of interferon titre. The measurement was conducted by using a system of L929 cell and vesicular stomatitis virus (VSV). Interferon titre was indicated as the reciprocal of the highest dilution of the sample which reduced plaque number by 50%. The results are shown in the following table.

Table

| Concentration (µg/ml) | Interferon titre (unit) |
|---|---|
| 5.0 | 320 |
| 1.65 | 320 |
| 0.5 | 160 |

As shown above, 320 units of interferon was induced by a solution having 5.0–1.65 µg/ml of the present compound, which concentration is relatively low.

2. Test in Vivo

Vaccinia virus was inoculated in a tail vein of a 4-week-old mouse. Six hours before inoculation, at the very time of inoculation and 18 and 42 hours after inoculation, 3'-cyano-2'-phenyl-2'-pyrroline-5'-spiro-6-penicillanic acid methyl ester was administered intraperitoneally in amounts of 7.8 mg/kg, 1.95 mg/kg, 0.49 mg/kg and 0.12 mg/kg respectively. On the 8th day from the date when virus was inoculated, poxes which appeared on the tail were numbered after dying and the number thereof was compared with that of the control mouse to judge the results. The results are shown in the following table.

Table

| Dose (mg/kg) | Number of pox | Inhibition percent (%) |
|---|---|---|
| 7.8 × 4 times | 11.2 | 54.3 |
| 1.95 × 4 times | 9.1 | 62.9 |

Table-continued

| Dose (mg/kg) | Number of pox | Inhibition percent (%) |
|---|---|---|
| 0.49 × 4 times | 16.0 | 34.7 |
| 0 × 4 times | 24.5 | — |

As shown above, the present compound has an excellent interferon inducibility.

Examles for preparing compounds of the present invention will be shown below.

EXAMPLE 1

3'-Cyano-2'-phenyl-2'-pyrroline-5'-spiro-6-penicillanic acid methyl ester

In 5 ml of chloroform was dissolved under heating 350 mg of phosphorus pentachloride in a 20 ml eggplant type flask. To the solution was added 440 mg of quinoline at room temperature to produce a white precipitate. After about 5 minutes, 500 mg of crystalline benzoylpenicillin methyl ester was added thereto as such. After addition, the mixture was stirred for about 1.5 hours and then evaporated in vacuo (2 mmHg.) to remove the solvent the give 6-chlorobenzylideneaminopenicillanic acid methyl ester. Without separating the compound produced, anhydrous tetrahydrofuran was added to the residue obtained after removing the solvent to produce a precipitate which was removed by quick filtration. The filtrate was cooled with an ice water. To the filtrate were added 0.27 ml of DBN and then 0.53 ml of acrylonitrile. The solution was stirred for about 1 hour and then a part of the solvent was removed by evaporation. The product was separated by preparative thin layer chromatography using silica gel to give 3'-cyano-2'-phenyl-2'-pyrroline-5'-spiro-6-penicillanic acid methyl ester melting at 196°–197° C in a 70% yield.

Ultraviolet absorption spectrum:
$\lambda_{max}^{EtOH}(\mu)$: 227, 320.
Infrared absorption spectrum:
$\nu_{max}^{Nujol}$(cm$^{-1}$): 3300, 2175, 1780.
Nuclear magnetic resonance spectrum (CDCl$_3$):
δ (ppm) : 1.50 (3H, singlet)
  1.66 (3H, singlet)
  3.30 and 3.55 (2H, AB-quartet, J=16.5 Hz)
  3.75 (3H, singlet)
  4.50 (1H, singlet)
  around 5.20 (1H)
  5.40 (1H, singlet)
  7.2–8.0 (5H, multiplet)
Elementary analysis for C$_{19}$H$_{19}$N$_3$O$_3$S — Calcd. : C 61.98, H 5.19, N 11.38, S 8.66 (%). Found : C 61.88, H 5.14, N 11.41, S 8.79 (%).
Mass spectrometry:
Parent peak (M+m/e) : 369.

EXAMPLE 2

3'-Cyano-2'-pyrroline-5'-spiro-6-penicillanic acid benzhydryl ester

In 5 ml of chloroform was dissolved under heating 350 mg of phosphorus pentachloride in a 20 ml eggplant type flask. To the solution was added 440 mg of quinoline at room temperature to produce a white precipitate. After about 5 minutes, 500 mg of crystalline benzoylpenicillin benzhydryl ester was added as such. After addition, the mixture was stirred for about 1.5 hours and then evaporated in vacuo (2 mmHg) to remove the solvent to give 6-chlorobenzylideneaminopenicillanic acid benzhydryl ester. Without separating the compound produced, 6 ml of anhydrous tetrahydrofuran was added to the residue obtained above after removing the solvent to produce a precipitate, which was subsequently removed by quick filtration. The filtrate was cooled with an ice water. To the filtrate were added 0.266 ml of DBN and then 0.53 ml of acrylonitrile. The solution was stirred for about 30 minutes and then a part of the solvent was removed by evaporation. The product was separated by preparative thin layer chromatography using silica gel to give 3'-cyano-2'-phenyl-2'-pyrroline-5'-spiro-6-penicillanic acid benzhydryl ester in a 52% yield.

Infrared absorption spectrum:
$\nu_{max}^{Nujol}$(cm$^{-1}$) : 3300, 2200, 1780, 1742, 1700.
Nuclear magnetic resonance spectrum (CDCl$_3$):
δ(ppm) : 1.30 (3 H, singlet)
  1.60 (3 H, singlet)
  3.20 and 3.50 (2H, AB-quartet, J=16 Hz)
  4.56 (1 H, singlet)
  around 5.20 (1 H)
  5.33 (1 H, singlet)
  6.95 (1 H, singlet)
  7.2–7.8 (15 H, multiplet)
Mass spectrometry:
Parent peak (M+m/e) : 521 (C$_{31}$H$_{27}$N$_3$O$_3$S).

EXAMPLE 3

3'-Cyano-2'-phenyl-2'-pyrroline-5'-spiro-7-deacetylcephalosporin trichloroethyl ester In 5 ml of chloroform was dissolved under heating 250 mg of phosphorus pentachloride in a 30 ml eggplant type flask. To the solution was added 330 mg of quinoline at room temperature to produce a white precipitate. After about 5 minutes, 500 mg of crystalline 7-benzoylaminodeacetylcephalosporin trichloroethyl ester was added as such. After addition, the mixture was stirred for about 1.5 hours and then evaporated in vacuo (2 mmHg) to remove the solvent to give 7-chlorobenzylideneaminodeacetylcephalosporin trichloroethyl ester. Without separating the compound produced, anhydrous tetrahydrofuran was added to the residue obtained above after removing the solvent to produce a precipitate, which was subsequently removed by quick filtration. The filtrate was cooled with an ice water. To the filtrate were added 0.2 ml of DBN and then 0.4 ml of acrylonitrile. The solution was stirred for about 1 hour and then a part of the solvent was removed by evaporation. The product was separated by preparative thin layer chromatography using silica gel to give 3'-cyano-2'-phenyl-2'-pyrroline-5'-spiro-7-deacetylcephalosporin trichloroethyl ester in a 45% yield.

Infrared absorption spectrum:
$\nu_{max}^{Nujol}$(cm$^{-1}$) : 3300, 2180, 1780, 1600.
Nuclear magnetic resonance spectrum (CDCl$_3$)
δ (ppm) : 2.21 (3 H, singlet)
  3.28 and 3.48 (2H, AB-quartet, J = 18 Hz) 4.79 (1 H, singlet)
  3.25 and 3.38 (2H, AB-quartet, J = 16 Hz)
  4.78 and 4.95 (2H, AB-quartet, J = 12 Hz)
Mass spectrometry:
Parent peak (M+ m/e): 482 (C$_{20}$H$_{15}$N$_3$O$_3$SCl$_3$, Cl$^{35}$).

EXAMPLE 4

3'-Carbomethoxy-2'-phenyl-2'-pyrroline-5'-spiro-6-penicillanic acid methyl ester Following the same procedures as in Example 1, 0.5 ml of methyl acrylate was subjected to reaction in place of acrylonitrile to give the desired compound in a 45% yield.

Infrared absorption spectrum:
$\nu_{max}^{Nujol}$ (cm$^{-1}$) : 3300, 1780, 1730, 1680.
Nuclear magnetic resonance spectrum (CDCl$_3$):
δ (ppm) : 1.50 (3 H, singlet)
  1.80 (3 H, singlet)
  2.62 and 2.94 (2H, AB-quartet, J = 14 Hz)
  3.65 (3 H, singlet)
  3.80 (3 H, singlet)
  4.60 (1 H, singlet)
  5.50 (1 H, singlet)
  730–8.20 (5H, multiplet)
Mass spectrometry:
Parent peak (M$^+$m/e) : 402.

EXAMPLE 5

3'-Cyano-2'-p-chlorophenyl-2'-pyrroline-5'-spiro-6-penicillanic acid methyl ester The reaction was effected in the same manner as in Example 1 except that p-chlorobenzoylpenicillin methyl ester was employed instead of the benzoylpenicillin methyl ester, thereby yielding the desired product. m.p. 180.5° C. yield 25%.

EXAMPLE 6

3'-Cyano-2'-p-nitrophenyl-2'-pyrroline-5'-spiro-6-penicillanic acid methyl ester The reaction was effected in the same manner as in Example 1 except that p-nitrobenzoylpenicillin methyl ester was employed instead of the benzoylpenicillin methyl ester, thereby yielding the desired product. m.p. 199° C, Yield 14%.

EXAMPLE 7

3'-Carboethoxy-2'-p-chlorophenyl-2'-pyrroline-5'-spiro-6-penicillanic acid methyl ester The reaction was effected in the same manner as in Example 1 except that p-chlorobenzoylpenicillin methyl ester and ethyl acrylate were employed instead of the benzoylpenicillin methyl ester and acrylonitrile respectively, thereby yielding the desired product. Yield 42%.

An oily substance,
Silica gel TLC (benzene: ethyl acetate = 5 : 1):
Rf = 0.54
Infrared absorption spectrum:
$\nu_{max}^{liq.}$ (cm$^{-1}$) : 3300, 1780, 1730.
Nuclear magnetic resonance spectrum (CDCl$_3$)
δ (ppm) : 1.15 (3 H, triplet, J = 7Hz) 1.47 (3 H, singlet)
  1.78 (3 H, singlet)
  2.16 and 2.86 (2 H, AB-quartet, J = 15 Hz)
  3.80 (3 H, singlet)
  4.10 (2 H, quartet, J = 7 Hz)
  4.61 (1 H, singlet)
  5.53 (1 H, singlet)
  7.2–8.2 (4 H, A$_2$B$_2$ type, multiplet)

EXAMPLE 8

3'-Cyano-2'-p-methoxyphenyl-2'-pyrroline-5'-spiro-6-penicillanic acid methyl ester The reaction was effected in the same manner as in Example I except that p-methoxy benzoylpenicillin methyl ester was employed instead of the benzoylpenicillin methyl ester, thereby yielding the desired product. Yield 15%

An oily substance
Silica gel TLC (benzene: ethyl acetate = 5 : 1):
Rf = 0.48
Infrared absorption spectrum:
$\nu_{max}^{liq.}$ (cm$^{-1}$): 3300, 2175, 1780.
Nuclear magnetic resonance spectrum (CDCl$_3$)
δ (ppm) : 1.47 (3 H, singlet)
  1.62 (3 H, singlet)
  3.30 (2 H, singlet)
  3.79 (3 H, singlet)
  3.85 (3 H, singlet)
  4.48 (1 H, singlet)
  5.38 (1 H, singlet)
  5.51 (1 H, singlet, –N<u>H</u>)
  6.85–8.00 (4 H, A$_2$B$_2$ type, multiplet)

EXAMPLE 9

3'-Carboethoxy-2'-phenyl-2'-pyrroline-5'-spiro-6-penicillanic acid methyl ester The reaction was effected in the same manner as in Example 1 except that ethyl acrylate was employed instead of the acrylonitrile, thereby yielding the desired product. Yield 30%.

An oily substance
Silica gel TLC (benzene : ethyl acetate = 5 : 1):
Rf = 0.53
Infrared absorption spectrum:
$\nu_{max}^{liq.}$ (cm$^{-1}$) : 3300, 1780, 1730.
Nuclear magnetic resonance spectrum (CDCl$_3$)
δ (ppm) : 1.07 (3 H, triplet, J = 7 Hz)
  1.42 (3 H, singlet)
  1.74 (3 H, triplet)
  2.62 and 2.80 (2 H, AB-quartet, J = 15 Hz)
  3.70 (3 H, singlet)
  4.04 (2 H, quartet, J = 7 Hz)
  4.57 (1 H, singlet)
  5.37 (1 H, singlet)
  5.49 (1 H, singlet)
  7.30–8.10 (4 H, multiplet)

EXAMPLE 10

3'-Cyano-2'-p-bromophenyl-2'-pyrroline-5=-spiro-6-penicillanic acid methyl ester The reaction was effected in the same manner as in Example 1 except that p-bromobenzoylpenicillin methyl ester was employed instead of the benzoylpenicillin methyl ester, thereby yielding the desired product. Yield 28% m.p. 175°–176° C.

EXAMPLE 11

3'-Cyano-2'-phenyl-2'-pyrroline-5'-spiro-6-penicillanic acid

In 10 ml of chloroform was dissolved under heating 380 mg of phosphorus pentachloride in a 30 ml eggplant type flask. To the solution was added 478 mg of quinoline at room temperature to produce a white precipitate. After about 5 minutes, 800 mg of benzoylpenicillin p-bromophenacyl ester was added as such. After addition, the mixture was stirred for about 1.5 hours and then evaporated in vacuo (2 mmHg) to remove the solvent to give 6-chlorobenzylideneaminopenicillanic acid p-bromophenacyl ester. Without separating the compound produced, 20 ml of anhydrous tetrahydrofuran was added to the residue obtained above after removing the solvent to produce a precipitate, which was subsequently removed by quick filtration. The filtrate was cooled with an ice water. To the filtrate were added 0.29 ml of DBN and then 0.58 ml of acrylonitrile. The solution was stirred for about 1 hour, ethyl acetate and subsequently water were added and the organic layer was washed with water and then dried over anhydrous magnesium sulfate. After the solvent was distilled off, the product was separated and purified by preparative thin layer chromatography using silica gel (benzene : ethyl acetate = 5 : 1) to give 3'-cyano-2'-phenyl-2'-pyrroline-5'-spiro-6-penicillanic acid p-bromophenacyl ester in a 28.5% yield as an oily substance.

Infrared absorption spectrum:
$\nu_{max}^{liq.}$ (cm$^{-1}$) : 3300, 2175, 1780, 1700.
Nuclear magnetic resonance spectrum (CDCl$_3$):
δ (ppm) : 1.70 (6 H, CH$_3$ × 2, singlet)
3.30 and 3.45 (2H, AB-quartet, J = 16 Hz)
4.56 (1 H, singlet)
5.25 (—NH)
5.35 (2 H, singlet)
5.36 (1 H, singlet)
7.20°–7.90 (9 H, multiplet)

In 0.5 ml of DMF was dissoled 80 mg of the spiro product thus obtained and 50 mg of potassium thiophenolate was added thereto. After 30 minutes, the resulting mixture was adjusted to pH 2.5 with 0.1% aqueous hydrochloric acid and extracted with ethyl acetate. The extract was dried over anhydrous magnesium sulfate and the solvent was distilled off. The crude product was separated and purified by perparative thin layer chromatography using silica gel (benzene : ethyl acetate = 1 : 1) to give 8 mg of 3'-cyano-2'-phenyl-2'-pyrroline-5'-sprio-6-penicillanic acid as an oily substance.

Ultraviolet absorption spectrum:
$\lambda_{max}^{EtOH}$ (μ) : 226.5, 317.
Infrared absorption spectrum:
$\nu_{max}^{CHCl_3}$ (cm$^{-1}$) : 3400–2400, 2200, 1785,1730.
Nuclear magnetic resonance spectrum (CDCl$_3$):
δ (ppm) :
1.59 (3 H, singlet)
1.65 (3 H, singlet)
3.30 and 3.50 (2 H, AB-quartet, J = 17 Hz)
4.47 (1 H, singlet)
5.19 (1 H, NH)
5.36 (1 H, singlet)
7.32–7.80 (5 H, multiplet)

EXAMPLE 12

3'-Cyano-2'-p-chlorophenyl-2'-pyrroline-5'-spiro-6-penicillanic acid

The reaction was effected in the same manner as in Example 11 except that p-chlorobenzoylpenicillin p-bromophenacyl ester was employed instead of the benzoylpenicillin p-bromophenacyl ester, thereby yielding 3'-cyano-2'-p-chlorophenyl-2'-pyrroline-5'-spriro-6-penicillanic acid p-bromophenacyl ester as an oily substance in a 32% yield.

Infrared absorption spectrum:
$\nu_{max}^{liq.}$ (cm$^{-1}$) : 3320, 2180, 1780, 1685.
Nuclear magnetic resonance spectrum (CDCl$_3$):
δ (ppm) : 1.65 (3 H, singlet)
1.68 (3 H, singlet)
3.35 and 3.49 (2 H, AB-quartet, J = 17 Hz)
4.51 (1 H, singlet)
5.20 (—NH)
5.30 (2 H, singlet)
5.33 (1 H, singlet)
7.35–7.88 (8 H, multiplet)

The spiro product thus obtained was reacted with potassium thiophenolate and treated in the same manner as in Example 11 to give the desired product in a 30% yield.

Infrared absorption spectrum:
$\nu_{max}^{CHLl_3}$ (cm$^{-1}$) : 3400–2400, 2190, 1780, 1728.
Nuclear magnetic resonance spectrum (CDLl$_3$)
δ (ppm) : 1.51 (3 H, singlet)
1.63 (3 H, singlet)
3.35 and 3.48 (2 H, AB-quartet, J = 17 Hz)
4.52 (1 H, singlet)
5.42 (1 H, singlet)
7.35–8.00 (5 H, multiplet)

What is claimed is:

1. A compound represented by the formula

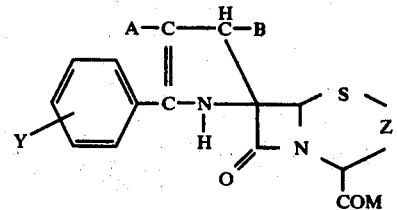

wherein Y represents a hydrogen atom, a halogen atom, a nitro group, an alkoxy group or an alkyl group; M represents a conventional protective group for a hydroxyl or carboxyl group; Z represents a group

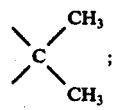

A represents a cyano group, a carboalkoxy group or a nitro group; and B represents a hydrogen atom, a cyano group, a carboalkoxy group or a nitro group.

2. A compound represented by the formula

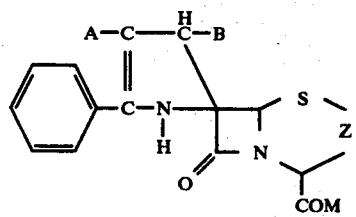

wherein M represents a hydroxyl group, an alkoxy group, a benzhydryloxy group or a trichloroethoxy group; Z represents a group

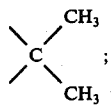

A represents a cyano group or a carbomethoxy group; and B represents a hydrogen atom or a carbomethoxy group.

3. The compound of claim 1 in which said protective group for a hydroxyl or carboxyl group is a methoxy group, a paramethoxybenzyloxy group, a bromophenacyloxy group, a benzhydryloxy group, a trimethylsilyloxy group or a chlorodimethylsilyloxy group.

4. 3'-Cyano-2'-phenyl-2'-pyrroline-5'-spiro-6-penicillanic acid methyl ester.

5. 3'-Cyano-2'-phenyl-2'-pyrroline-5'-spiro-6-penicillanic acid benzhydryl ester.

6. 3'-Carbomethoxy-2'-phenyl-2'-pyrroline-5'-spiro-6-penicillanic acid methyl ester.

* * * * *

UNITED STATES PATENT AND TRADEMARK OFFICE
CERTIFICATE OF CORRECTION

PATENT NO. : 4,064,137
DATED : December 20, 1977
INVENTOR(S) : KOICHI HIRAI et al It is certified that error appears in the above-identified patent and that said Letters Patent are hereby corrected as shown below:

Column 4, line 12: replace "6 - 7" with ---6- or 7---.

Column 7, line 56: after "cyano", insert --- -2'-phenyl---.

Column 10, line 51: replace "5=" with ---5'---.

Column 12, line 19: replace "(CDLl$_3$)" with ---(CDCl$_3$)---.

Signed and Sealed this

Third Day of October 1978

[SEAL]

Attest:

RUTH C. MASON
Attesting Officer

DONALD W. BANNER
Commissioner of Patents and Trademarks